(12) United States Patent
Everett et al.

(10) Patent No.: US 8,913,793 B2
(45) Date of Patent: *Dec. 16, 2014

(54) METHOD OF BIOIMAGE DATA PROCESSING FOR REVEALING MORE MEANINGFUL ANATOMIC FEATURES OF DISEASED TISSUES

(71) Applicant: Carl Zeiss Meditec, Inc., Dublin, CA (US)

(72) Inventors: Matthew J. Everett, Livermore, CA (US); Scott A. Meyer, Livermore, CA (US); Paul F. Stetson, Piedmont, CA (US); Yan Zhou, Pleasanton, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/787,557

(22) Filed: Mar. 6, 2013

(65) Prior Publication Data

US 2013/0281841 A1 Oct. 24, 2013

Related U.S. Application Data

(63) Continuation of application No. 13/488,280, filed on Jun. 4, 2012, now Pat. No. 8,416,991, which is a
(Continued)

(51) Int. Cl.
*G06K 9/00* (2006.01)
(Continued)

(52) U.S. Cl.
CPC ............... *A61B 5/0066* (2013.01); *G06T 19/00* (2013.01)
USPC ........................... 382/106; 356/479; 600/425

(58) Field of Classification Search
CPC ............... G06T 1/00; A61B 1/00; G01B 1/00
USPC .......... 382/106, 128–134; 600/101–105, 118, 600/356, 383, 400–402, 442, 445, 459, 587, 600/592, 595, 425; 351/204; 356/479, 482; 128/920, 922
See application file for complete search history.

(56) References Cited

U.S. PATENT DOCUMENTS

| | | |
|---|---|---|
| 4,838,679 A | 6/1989 | Bille |
| 5,293,871 A | 3/1994 | Reinstein et al. |

(Continued)

FOREIGN PATENT DOCUMENTS

| | | |
|---|---|---|
| CA | 2390072 A | 12/2003 |
| EP | 0415683 A2 | 3/1991 |

(Continued)

OTHER PUBLICATIONS

Chung et al., "Choroidal Thickness in Polypoidal Choroidal Vasculopathy and Exudative Age-related Macular Degeneration", Ophthalmology, vol. 118, No. 5, May 2011, pp. 840-845.

(Continued)

*Primary Examiner* — Abolfazl Tabatabai
(74) *Attorney, Agent, or Firm* — Morrison & Foerster LLP

(57) ABSTRACT

The present invention discloses a method for generating elevation maps or images of a tissue layer/boundary with respect to a fitted reference surface, comprising the steps of finding and segmenting a desired tissue layer/boundary; fitting a smooth reference surface to the segmented tissue layer/boundary; calculating elevations of the same or other tissue layer/boundary relative to the fitted reference surface; and generating maps of elevation relative to the fitted surface. The elevation can be displayed in various ways including three-dimensional surface renderings, topographical contour maps, contour maps, en-face color maps, and en-face grayscale maps. The elevation can also be combined and simultaneously displayed with another tissue layer/boundary dependent set of image data to provide additional information for diagnostics.

18 Claims, 6 Drawing Sheets

Related U.S. Application Data continuation of application No. 13/283,445, filed on Oct. 27, 2011, now Pat. No. 8,208,688, which is a continuation of application No. 12/709,234, filed on Feb. 19, 2010, now Pat. No. 8,073,202, which is a continuation of application No. 11/223,549, filed on Sep. 9, 2005, now Pat. No. 7,668,342.

(51) Int. Cl.
*A61B 5/00* (2006.01)
*G06T 19/00* (2011.01)
*G01B 9/02* (2006.01)
*A61B 5/05* (2006.01)

(56) References Cited

U.S. PATENT DOCUMENTS

| | | | |
|---|---|---|---|
| 5,321,501 A | 6/1994 | Swanson et al. | |
| 5,459,570 A | 10/1995 | Swanson et al. | |
| 5,465,147 A | 11/1995 | Swanson | |
| 5,562,095 A | 10/1996 | Downey et al. | |
| 5,861,955 A * | 1/1999 | Gordon | 356/511 |
| 5,921,926 A | 7/1999 | Rolland et al. | |
| 5,975,697 A | 11/1999 | Podoleanu et al. | |
| 6,165,142 A | 12/2000 | Bar | |
| 6,201,989 B1 | 3/2001 | Whitehead et al. | |
| 6,260,968 B1 | 7/2001 | Stark et al. | |
| 6,609,793 B2 | 8/2003 | Norrby et al. | |
| 6,769,769 B2 | 8/2004 | Podoleanu et al. | |
| 6,927,860 B2 | 8/2005 | Podoleanu et al. | |
| 7,145,661 B2 | 12/2006 | Hitzenberger | |
| 7,194,117 B2 | 3/2007 | Kaufman et al. | |
| 7,301,644 B2 | 11/2007 | Knighton et al. | |
| 7,364,296 B2 | 4/2008 | Miller et al. | |
| 7,365,856 B2 | 4/2008 | Everett et al. | |
| 7,433,046 B2 | 10/2008 | Everett et al. | |
| 7,466,423 B2 | 12/2008 | Podoleanu et al. | |
| 7,474,407 B2 | 1/2009 | Gutin | |
| 7,497,575 B2 | 3/2009 | Huang et al. | |
| 7,505,142 B2 | 3/2009 | Knighton et al. | |
| 7,616,799 B2 | 11/2009 | Ramamurthy et al. | |
| 7,659,990 B2 | 2/2010 | Knighton et al. | |
| 7,668,342 B2 | 2/2010 | Everett et al. | |
| 7,798,641 B2 | 9/2010 | Bille | |
| 7,830,525 B2 | 11/2010 | Buckland et al. | |
| 7,884,945 B2 | 2/2011 | Srinivasan et al. | |
| 7,901,080 B2 | 3/2011 | Hauger et al. | |
| 7,924,429 B2 * | 4/2011 | Knighton et al. | 356/479 |
| 2003/0199769 A1 | 10/2003 | Podoleanu et al. | |
| 2004/0036838 A1 | 2/2004 | Podoleanu et al. | |
| 2004/0133112 A1 | 7/2004 | Rajadhyaksha | |
| 2004/0233457 A1 | 11/2004 | Podoleanu et al. | |
| 2004/0239938 A1 | 12/2004 | Izatt | |
| 2005/0048044 A1 | 3/2005 | Schwartz et al. | |
| 2005/0096515 A1 | 5/2005 | Geng | |
| 2005/0254009 A1 | 11/2005 | Baker et al. | |
| 2006/0066869 A1 | 3/2006 | Ueno et al. | |
| 2006/0072424 A1 | 4/2006 | Everett et al. | |
| 2006/0119858 A1 | 6/2006 | Knighton et al. | |
| 2006/0132790 A1 | 6/2006 | Gutin | |
| 2006/0164639 A1 | 7/2006 | Horn et al. | |
| 2006/0164653 A1 | 7/2006 | Everett et al. | |
| 2006/0187462 A1 | 8/2006 | Srinivasan et al. | |
| 2006/0228011 A1 | 10/2006 | Everett et al. | |
| 2007/0012886 A1 | 1/2007 | Tearney et al. | |
| 2007/0025642 A1 | 2/2007 | Buckland et al. | |
| 2007/0030483 A1 | 2/2007 | Everett et al. | |
| 2007/0103693 A1 | 5/2007 | Everett et al. | |
| 2007/0115481 A1 | 5/2007 | Toth et al. | |
| 2007/0216909 A1 | 9/2007 | Everett et al. | |
| 2010/0111373 A1 | 5/2010 | Chin et al. | |
| 2011/0299034 A1 | 12/2011 | Walsh et al. | |
| 2012/0075584 A1 | 3/2012 | Stetson | |
| 2013/0281841 A1 | 10/2013 | Everett et al. | |

FOREIGN PATENT DOCUMENTS

| | | |
|---|---|---|
| WO | 2004/043245 A1 | 5/2004 |
| WO | 2004/102112 A1 | 11/2004 |

OTHER PUBLICATIONS

Gregori et al., "Imaging Drusen With Spectral Domain Optical Coherence Tomography", Invest Ophthalmol Vis Sci, vol. 49, E-Abstract 4234, 2008, 2 pages.

Hartnett et al., "Classification of Retinal Pigment Epithelial Detachments Associated with Drusen", Graefes Arch Clin Exp Ophthalmol, vol. 230, 1992, pp. 11-19.

Khanifar et al., "Drusen Ultrastructure Imaging with Spectral Domain Optical Coherence Tomography in Age-related Macular Degeneration", Ophthalmology, vol. 115, No. 11, Nov. 2008, pp. 1883-1890.

Lee et al., "Automated Characterization of Pigment Epithelial Detachment using Optical Coherence Tomography", 2011 ARVO Poster Abstract Program #1317, Poster #A254, 2011, 27 pages.

Lumbroso et al., "Morphologic Differences, According to Etiology, in Pigment Epithelial Detachments by Means of En Face Optical Coherence Tomography", Retina, The Journal of Retinal and Vitreous Diseases, vol. 31, No. 3, 2011, pp. 553-558.

Zayit-Soudry, "Retinal Pigment Epithelial Detachment", Survey of Ophthalmology, vol. 52, No. 3, May-Jun. 2007, pp. 227-243.

Extended European Search Report (includes European Search Report and European Search Opinion) received for European Patent Application No. 13151051.3, mailed on Jul. 1, 2013, 7 pages.

Non-Final Office Action received for U.S. Appl. No. 13/240,701, mailed on Nov. 7, 2013, 9 pages.

Wilkins et al., "Characterization of Epiretinal Membranes Using Optical Coherence Tomography", Ophthalmology, vol. 103, No. 12, Dec. 1996, pp. 2142-2151.

Optovue Inc.,"RTVue-I00—In-Vivo Histology (Fourier Domain OCT)", Oct. 2006 Brochure by Optovue Inc., 2006, 6 pages.

Ortiz et al., "In Vivo Human Crystalline Lens Topography", Biomedical Optics Express, vol. 3, No. 10, Oct. 1, 2012, pp. 2471-2488.

OTI Ophthalmic Technologies Inc., "OCT/SLO Combination Imaging System", Sep. 2005 User Manual by OTI Ophthalmic Technologies Inc., 2005, 79 pages.

Paunescu et al., "Reproducibility of Nerve Fiber Thickness, Macular Thickness, and Optic Nerve Head Measurements Using StratusOCT", Investigatative Ophthalmology & Visual Science, vol. 45, No. 6, Jun. 2004, pp. 1716-1724.

Puliafito, CA, "Summary and Significance", American Academy of Ophthalmology Subspecialty Day on retina, Section X Ocular Imaging, New Orleans, Oct. 23, 2004, 16 pages.

Sacu, S., "Imaging and Pigment Epithelial Disease Using Three dimensional (3D) Ultrahigh Resolution (UHR) Optical Coherence Tomography (OCT)", ARVO Annual Meeting, Program#/Poster#: 2563/B116, printed from website, http://www.abstractsonline.comlviewer/ViewAbstractPrintFriendly on Jul. 26, 2005, May 3, 2005, 1 page.

Sadda et al., "Automated Detection of Clinically Significant Macular Edema by Grid Scanning Optical Coherence Tomography", Ophthalmology, vol. 113, No. 7, Jul. 2006, pp. 1187-1196.

Satoh et al., "Accommodative Changes in Human Eye Observed by Kitasato Anterior Segment Optical Coherence Tomography", The Official International Journal of the Japanese Ophthalmological Society, vol. 57, 2013, pp. 113-119.

Schmidt-Erfurth et al., "Three-Dimensional Ultrahigh-Resolution Optical Coherence Tomography of Macular Diseases, Investigative", Ophthalmology & Visual Science, vol. 46, No. 9, Sep. 2005, pp. 3393-3402.

Schmidt-Erfurth et al., "Three-Dimensional Ultrahigh Resolution Optical Coherence Tomography (3D UHR OCT): A Video Presentation", ARVO Annual Meeting, Program#/Poster#: 1115,, printed from website, http://www.abstractsonline.comiviewerNiewAbstractPrintFriendly on Jul. 26, 2005, May 2, 2005, 1 page.

Scholda et al., "Visualization of the Vitreoretinal Interface Using Three-Dimensional Ultrahigh Resolution Optical Coherence

(56) References Cited

OTHER PUBLICATIONS

Tomography", ARVO Annual Meeting, Program#/Poster#: 1054,, printed from website, http://www.abstractsonline.comiviewerNiewAbstractPrintFriendly on Jul. 26, 2005, May 2, 2005, 1 page.
Sharp, P F., "The Scanning Laser Ophthalmoscope—a Review of its role in Bioscience and Medicine", Physics in Medicine and Biology, vol. 49, 2004, pp. 1085-1096.
Srinivasan et al., "Intraretinal Thickness Mapping using Three Dimensional, High-Speed Ultrahigh Resolution OCT", ARVO Annual Meeting, Program#/ Poster#: 1113, printed from website, http://www.abstractsonline.comiviewerNiewAbstractPrintFriendly on Jul. 26, 2005, May 2, 2005, 1 page.
Swanson et al., "In Vivo Retinal Imaging by Optical Coherencetomography", Optics Letters vol. 18 No. 21, Nov. 1, 1993, pp. 1864-1866.
Werner et al., "Three-Dimensional Retinal Imaging With High Speed and High Resolution OCT", ARVO Annual Meeting, Program#/ Poster#: 1052, printed from website, http://www.abstractsonline.comlviewer/ViewAbstractPrintFriendly on Jul. 26, 2005, May 2, 2005, 1 page.
Wojkowski, M., "Three-Dimensional Retinal Imaging with High-Speed Ultrahigh-Resolution Optical Coherence Tomography", American Journal of Ophthalmology, Ophthalmic Publ., Chicago, Illinois, Sep. 2004, 13 pages.
Wojtkowski et al., "Real-Time and Static in Vivo Ophthalmic Imaging by Spectral Optical Coherence Tomography", Proceedings of SPIE, vol. 5314, 2004, pp. 126-131.
Wojtkowski et al., "Three-Dimensional Retinal Imaging with High-Speed Ultrahigh-Resolution Optical Coherence Tomography", Ophthalmology, vol. 112, No. 10, Oct. 2005, pp. 1734-1746.
Wojtkowski et al., "Ophthalmic Imaging by Spectral Optical Coherence Tomography", American Journal of Ophthalmology, Ophthalmic Publ., Chicago, IL vol. 138 No. 3, Sep. 2004, pp. 412-419.
Wojtkowski, Maciej, "Good Quality medical Imaging by Ultra-Fast Spectral OCT Device", MIT Presentation, Oct. 22, 2003, 36 pages.
Wu et al., "Visual Acuity, Optical Components, and Macular Abnormalities in Patients with a History of Retinopathy of Prematurity", The American Academy of Ophthalmology, vol. 119, No. 9, Sep. 2012, pp. 1907-1916.
Knighton et al., U.S. Appl. No. 60/632,387, filed Dec. 2, 2004, entitled "Enhanced Optical Coherence Tomography for Anatomical Mapping", 26 pages.
Final Office Action received for U.S. Appl. No. 13/240,701, mailed on Jul. 15, 2013, 9 pages.
Office Action received for European Patent Application No. 05815426.1, mailed on Jan. 13, 2011, 3 pages.
International Search Report and Written Opinion received for PCT Patent Application No. PCT/EP2005/012801, mailed on on Mar. 23, 2006, 9 pages.
Non Final Office Action received for U.S. Appl. No. 12/644,526, mailed on Sep. 1, 2010, 18 pages.
Notice of Allowance received for U.S. Appl. No. 12/644,526, mailed on Feb. 7, 2011, 9 pages.
Notice of Allowance received for U.S. Appl. No. 11/717,263, mailed on Mar. 23, 2010, 6 pages.
Notice of Allowance received for U.S. Appl. No. 12/644,526, mailed on Feb. 24, 2011, 7 pages.
Non Final Office Action received for U.S. Appl. No. 12/822,054, mailed on Apr. 5, 2011, 12 pages.
Notice of Allowance received for U.S. Appl. No. 12/822,054, mailed on Jul. 26, 2011, 21 pages.
Non-Final Office Action received for U.S. Appl. No. 13/043,401, mailed on Mar. 26, 2012, 22 pages.
Notice of Allowance received for U.S. Appl. No. 13/043,401, mailed on Jul. 27, 2012, 7 pages.
Non Final Office Action received for U.S. Appl. No. 13/240,701, mailed on Dec. 21, 2012, 9 pages.

Alam et al., Clinical Application of Rapid Serial Fourier-Domain Optical Coherence Tomography for Macular Imaging Ophthalmology, vol. 113, No. 8, Aug. 2006, pp. 1425-1431.
Bartsch et al., "Optical Coherence Tomography: Interpretation Artifacts and New Algorithm", Proc. SPIE Medical Imaging 2004: Image Processing, vol. 5370, 2004, pp. 2140-2151.
Bajraszewski et al., "Three-Dimensional in Vivo Imaging by Spectral OCT", Proc. of SPIE, vol. 5316, 2004, pp. 226-232.
Baroni et al., "Towards Quantitative Analysis of Retinal Features in Optical Coherence Tomography", Medical Engineering & Physics, vol. 29, 2007, pp. 432-441.
Boppart et al., "Noninvasive Assessment of the Developing Xenopus Cardiovascular System Using Optical Coherence Tomography", Proceedings of the National Academy of Sciences of the United States of America, vol. 94, Apr. 1997, pp. 4256-4261.
Boppart, Stephen Allen, "Surgical Diagnostics, Guidance, and Intervention using Optical Coherence Tomography", Massachusetts Institute of Technology, May 1998, 237 pages.
Bower et al., "Rapid Volumetric Imaging of the Human Retina in vivo Using a Low-Cost, Spectral-Domain Optical Coherence Tomography System", ARVO Annual Meeting, Program#/Poster#: 1050, printed from website, http://www.abstractsonline.comiviewerNiewAbstractPrintFriendly on Jul. 26, 2005, May 2, 2005, 2 pages.
Burgoyne et al., "Three-Dimensional Reconstruction of Normal and Early Glaucoma Monkey Optic Nerve Head Connective Tissues", Investigative Ophthalmology & Visual Science, Dec. 2004, vol. 45, No. 12, 2004, pp. 4388-4399.
Carl Zeiss Meditec, Inc., "STRATUS OCT1M—Model 3000", Apr. 2004 User Manual by Carl Zeiss Meditec, Inc., 190 pages.
Costa et al., "Retinal Assessment Using Optical Coherence Tomography", Progress in Retinal and Eye Research, vol. 25, 2006, pp. 325-353.
De Boer et al., "Improved Signal-to-Noise Ratio in Spectral-Domain Compared with Time-Domain Optical Coherence Tomography", Optics Letters, vol. 28, No. 21, Nov. 1, 2003, pp. 2067-2069.
De Boer et al., "Ultra-High Speed and Ultra-High Resolution Structural, Flow Velocity, and Polarization Sensitive Sd/Fd-Oct and the Human Retina", ARVO Annual Meeting, Program#/Poster#: 1116, printed from website, http://www.abstractsonline.comiviewerNiewAbstractPrintFriendly on Jul. 26, 2005, May 2, 2005, 2 pages.
Dubois et al., "High-Resolution Three-Dimensional Imaging inside Biological Media Using White-Light Interference Microscopy", Proceedings of SPIE, vol. 5140, 2003, pp. 43-50.
Fercher et al., "Optical Coherence Tomography—Principles and Applications", Reports on Progress in Physics, vol. 66, 2003, pp. 239-303.
Ferguson et al., "Enhanced Retinal Imaging With Tracking Optical Coherence Tomography (TOCT)", ARVO Annual Meeting, Program#/Poster#: 1118, printed from website, http://www.abstractsonline.comlviewer/ViewAbstractPrintFriendly on Jul. 26, 2005, May 2, 2005, 1 page.
Fujimoto, JG., "New Technology for Optical Coherence Tomography", table of contents title Advances in High Resolution and Spectral OCr, Ocular Imaging 2005, Palm Beach, Florida, Dec. 3-4, 2004, 8 pages.
Gregori et al., "3-D OCT Maps in Retinal Pathologies", ARVO Annual Meeting, Program#/ Poster#: 1055, printed from website, http://www.abstractsonline.com/viewer/ViewAbstractPrintFriendly on Jul. 26, 2005, May 2, 2005, 1 page.
Heidelberg Engineering, "Bringing two views together Spectralis 1M HRA + OCT", Nov. 2006 Brochure by Heidelberg Engineering, 2006, 6 pages.
Hitzenberger et al., "Three-Dimensional Imaging of the Human Retina by High-Speed Optical Coherence Tomography", Optics Express, vol. 11, No. 21, Oct. 20, 2003, pp. 2753-2761.
Srivastava et al., "Differential Geometric Metrics Characterizing Optical Coherence Tomography Data", Unpublished U.S. Appl. No. 13/744,911, filed Jan. 18, 2013.
Huang et al., "Optical Coherence Tomography", Science, vol. 254, Nov. 22, 1991, pp. 1178-1181.

(56) References Cited

OTHER PUBLICATIONS

Ikuno et al., "Ocular Risk Factors for Choroidal Neovascularization in Pathologic Myopia", Investigative Ophthalmology & Visual Science, vol. 51, No. 7, Jul. 2010, pp. 3721-3725.
Izatt et al., "Ophthalmic Diagnostics using Optical Coherence Tomography,", Ophthalmic Technologies IIL SPIE, Los Angeles, CA, 1877, Jan. 16-18, 1993, pp. 136-144.
Jiao et al., "Simultaneous Acquisition of Sectional and Fundus Ophthalmic Images with Spectral-Domain Optical Coherence Tomography", Optics Express, vol. 13, No. 2, Jan. 24, 2005, pp. 444-452.
Jiao et al., "Macula Mapping and Simultaneous Acquisition of Sectional and Fundus Ophthalmic Images With Three-Dimensional Spectral-Domain Optical Coherence Tomography", ARVO Annual Meeting, Program#/Poster#: 1114, printed from website, http://www.abstractsonline.comlviewer/ ViewAbstractPrintFriendly on Jul. 26, 2005, May 2, 2005, 1 page.
Jiao et al., "Simultaneous Acquisition of Sectional and Fundus Images with Spectral-Domain Optical Coherence Tomography", Photonics West, Ophthalmic Technologies XV, Program #5688-81, Powerpoint presentation, Jan. 22, 2005, 21 pages.
Kinori et al., "Enhanced S-Cone Function with Preserved Rod Function: A New Clinical Phenotype", Molecular Vision, vol. 17, Aug. 18, 2011, pp. 2241-2247.
Ko et al., "Three Dimensional Retinal Imaging of Small Animals With High-speed, Ultrahigh Resolution Optical Coherence Tomography", ARVO Annual Meeting, Program#/Poster#: 1051, printed from website, http://www.abstractsonline.comiviewerNiewAbstractPrintFriendly on Jul. 26, 2005, May 2, 2005, 1 page.
Koendrink et al., "The Structure of Relief", Advances in Imaging and Electron Physics, vol. 103, 1998, pp. 65-150.
Koendrink et al., "Two-Plus-One-Dimensional Differential Geometry", Pattern Recognition Letters, vol. 15, May 1994, pp. 439-443.
Koozekanani et al., "Tracking the Optic Nervehead in OCT Video Using Dual Eigenspaces and an Adaptive Vascular Distrubution Model", IEEE Transactions on Medical Imaging, vol. 22, No. 12, Dec. 2003, pp. 1519-1536.
Lee et al., "In vivo Optical Frequency Domain Imaging of Human Retina and Choroid", Optics Express, vol. 14, No. 10, May 15, 2006, pp. 4403-4411.
Leitgeb et al., "Performance of Fourier Domain vs. Time Domain Optical Coherence Tomography", Optics Express vol. 11, No. 8, Apr. 21, 2003, pp. 889-894.
Leitgeb et al., "Ultrahigh Resolution Fourier Domain Optical Coherence Tomography", Optics Express, vol. 12, No. 10, May 17, 2004, pp. 2156-2165.
Mujat et al., "Retinal Nerve Fiber Layer Thickness Map Determined from Optical Coherence Tomography Images", Optics Express, vol. 13, No. 23, Nov. 14, 2005, pp. 9480-9491.
Nassif et al., "In Vivo Human Retinal Imaging by Ultrahigh-Speed Spectral Domain Optical Coherence Tomography", Optics Letters, vol. 29, No. 5, Mar. 1, 2004, pp. 480-482.
Nassif et al., "In Vivo High-Resolution Video-Rate Spectral-Domain Optical Coherence Tomography of the Human Retina and Optic Nerve", Optics Express vol. 12, No. 3, Feb. 9, 2004, pp. 367-376.
Ohno-Matsui et al., "Intrachoroidal Cavitation in Macular Area of Eyes With Pathologic Myopia", American Journal of Ophthalmology, vol. 154, No. 2, Aug. 2012, pp. 382-393.
Ophthalmic Technologies Inc., "OT! OCT/SLO Combination Imaging System", Nov. 2005 Brochure by on Ophthalmic Technologies Inc, 2005, 6 pages.
Non Final Office Action received for U.S. Appl. No. 12/709,234, mailed on Feb. 16, 2011, 6 pages.
Notice of Allowance received for U.S. Appl. No. 12/709,234, mailed on Jul. 28, 2011, 10 pages.
Notice of Allowance received for U.S. Appl. No. 13/283,445, mailed on Feb. 23, 2012, 10 pages.
Notice of Allowance received for U.S. Appl. No. 13/488,280, mailed on Dec. 10, 2012, 10 pages.
Adaikkappan et al., "Evaluation of Carotid Atherosclerosis by B'Mode Ultrasonographic Study in Hypertensive Patients Compared with Normotensive Patients", Ind. J. Radiol. Imag., vol. 12, No. 3, 2002, pp. 365-368.
Choma et al., "Sensitivity Advantage of Swept Source and Fourier Domain Optical Coherence Tomography", Optics Express, vol. 11, No. 18, Sep. 8, 2003, pp. 2183-2189.
Guirao et al., "Corneal Wave Aberration from Videokeratography: Accuracy and Limitations of the Procedure" J. Opt. Soc. Am. A, vol. 17, No. 6, Jun. 2000, pp. 955-965.
Ishikawa et al., "Macular Segmentation with Optical Coherence Tomography," Investigative Ophthalmology & Visual Science, vol. 46, No. 6, 2005, pp. 2012-2017.
R.H. Webb, "Confocal Optical Microscopy", Rep. Prog. Phys., vol. 59, 1996, pp. 427-471.
Zhou et al., "Mapping Retinal Thickness and Macular Edema by High-Speed Three Dimensional Optical Coherence Tomography", Ophthalmic Technologies XIV, Proceedings of SPIE (Bellingham, Washington), vol. 5314, 2004, pp. 119-125.

\* cited by examiner

METHOD OF BIOIMAGE DATA PROCESSING FOR REVEALING MORE MEANINGFUL ANATOMIC FEATURES OF DISEASED TISSUES

PRIORITY

This application is a continuation of U.S. patent application Ser. No. 13/488,280, filed Jun. 4, 2012, which is in turn a continuation of U.S. patent application Ser. No. 13/283,445, filed Oct. 27, 2011 (now U.S. Pat. No. 8,208,688), which is in turn a continuation of U.S. patent application Ser. No. 12/709,234, filed Feb. 19, 2010 (now U.S. Pat. No. 8,073,202), which is in turn a continuation of U.S. patent application Ser. No. 11/223,549, filed Sep. 9, 2005 (now U.S. Pat. No. 7,668,342), the disclosures of which are herein incorporated by reference in their entirety.

TECHNICAL FIELD OF THE INVENTION

One or more embodiments of the present invention relate generally to methods for optical imaging of biological samples and for processing such images. In particular, the invention is a method for processing a three-dimensional image data set to generate elevation maps of tissue layers relative to a fitted smooth surface, which can provide more diagnostic information than a pure tissue layer thickness map. Maps of elevation may be embodied as three-dimensional surface renderings of elevation, topographical maps, or as color or grayscale maps.

BACKGROUND OF THE INVENTION

Measurement of biological tissue surface contour or layer thickness can provide useful diagnostic information in various applications. For example, arterial plaque thickness is related to the progress of atherosclerosis, carotid vessel wall thickness is also an indicator of cardiovascular disease risk; epidermal layer thickness is an indicator of burn severity.

In ophthalmology, retinal thickness may be abnormally large in cases of retinal edema or traction by membranes in the vitreous humor. On the other hand, the retina may appear thin in cases of atrophic degeneration, chorioretinitis, or trauma to the retina. Meanwhile, changes in retinal thickness may be localized or extend over large areas. In certain cases, the overall contour of the retina may become abnormal. For example, pronounced myopia, particularly due to posterior staphylomas, may create a highly concave retina. Detachment of the retinal pigment epithelium (RPE), subretinal cysts, or subretinal tumors may produce a relative convexity of the retina. Therefore, mapping the retina contour or retinal thickness makes it possible to determine the extent and severity of such conditions and to monitor progress of treatment.

In the past, there are a number of well-established biomedical imaging techniques that have been used for three-dimensional anatomical mapping of the eye, especially the retina, including optical coherence tomography (Zhou, Q. et al. (2004). "Mapping retinal thickness and macular edema by high-speed three-dimensional optical coherence tomography". Ophthalmic Technologies XIV, SPIE, 5314: 119-125), ultrasound (see for example, U.S. Pat. Nos. 5,293,871, 5,562,095), and confocal microscopy (see for example, U.S. Pat. No. 4,838,679; R. H. Webb (1996) "Confocal optical microscopy" *Rep. Prog. Phys.* 59 427-471). The three-dimensional data set has also been analyzed to identify layered structures in the tissue using a variety of approaches to image segmentation. (see for example, D. G. Bartsch, et al., (2004) "Optical coherence tomography: interpretation artifacts and new algorithm", *Proc. SPIE Medical Imaging* 2004: *Image Processing*, 5370: 2140-2151; H. Ishikawa, et al., (2005) "Macular Segmentation with Optical Coherence Tomography". *Invest Ophthalmol Vis Sci.;* 46: 2012-201).

These prior art methods measured and/or generated a map of a tissue layer thickness by searching for the borders of the tissue layer structures, figuring out the inner and outer boundaries and then finding the distance between the inner and outer boundaries. However, a major issue associated with a tissue layer thickness map is that it sometimes cannot reveal the diagnostically more meaningful features of a diseased part of the tissue. For example, retina thickness is defined as the vertical distance between the RPE (retinal pigment epithelium) 102 and the ILM (inner limiting membrane) 104 as shown in FIG. 1. A sharp bump 106 of the retina will often be associated with a rise in the RPE 102 as well as the formation of a lesion 108 below the RPE 102, such that the RPE also has a broad rise. As a result, a retina thickness map such as the color coded one shown in FIG. 2, which corresponds to FIG. 1, cannot reveal the substantially raised bump. In fact, the color coded thickness map shows that the thickness will only slightly increase near the bump but then return to normal over it. On the other hand, although a topographic map or contour of the RPE or ILM may reveal the sharp bump better for this illustrated case than the retina thickness map, it would include both the sharp bump and the broader warping of the RPE boundary, making it difficult to separate the effect of the disease from the overall shape of the RPE boundary.

In light of the above, there is a need in the art for a method for generating elevation maps with respect to a reference fitted surface and for using the reference surface as a means of locating three-dimensionally a tissue or a layer or boundary of a tissue such as the retina, in order to provide diagnostically more meaningful information about potential diseased tissue.

The present invention is a novel and non-obvious method wherein a fitted reference surface is used to create an elevation map or image of a tissue layer/boundary with respect to the fitted reference surface. Use of such a fitted surface can minimize the perturbations of the surface associated with disease so as to approximate the tissue surface that would exist if the tissue were normal. By using such a fitted surface, either of the tissue boundary being measured, or a different boundary, the effect of disease or injury is isolated from the overall shape of the tissue of interest, providing improved diagnostic information. In addition to various ways to display the elevation data relative to the fitted reference surface, the invention also combines the elevation data with other maps or images in order to provide more meaningful information for diagnostics.

SUMMARY OF THE INVENTION

One or more embodiments of the present invention satisfy one or more of the above-identified needs in the art. In particular, one embodiment of the present invention is a method for generating elevation maps or images of a tissue layer/boundary with respect to the location of a fitted reference surface, comprising the steps of finding and segmenting a desired tissue layer/boundary; fitting a smooth reference surface to the segmented tissue layer/boundary; calculating elevations of the same or other tissue layer/boundary relative to the fitted reference surface; and generating maps of elevation relative to the fitted surface.

One aspect of the present invention is to display the elevation in various ways including three-dimensional surface renderings, topographical contour maps, contour maps, en-face color maps, and en-face grayscale maps.

Another aspect of the present invention is to combine and hence simultaneously display on the same map and/or image two sets of data with one set from the elevation relative to a fitted reference surface and the other set from a tissue layer/boundary dependent information, including, for example, actual thickness of a tissue layer, and image signal strength such as reflectance from an OCT system, birefringence from a polarization sensitive OCT system or a scanning laser polarimetry system, and intensity from a confocal imaging system.

Another aspect of the present invention is to perform the fitting to obtain the reference surface in a number of ways, including using a second-order polynomial fit, or using Zernike or Chebyshev or other polynomials, or Bessel functions, or a portion of a sphere or spheroid. Additionally, the fitting can also be performed by excluding certain portions of the tissue layer/boundary, i.e. the regions of diseased tissue, from the determination of the fitted reference surface, or fitting on more than one region of the tissue layer/boundary or smoothing/filtering a tissue layer/boundary.

Still another aspect of the invention is to locate the general tissue layer/boundary contour for subsequent scans, which need to follow the tissue contour closely.

Additional aspects of the invention will be set forth in part in the description which follows. It is to be understood that both the foregoing general description and the following detailed description are exemplary and explanatory only and are not restrictive of the invention, as claimed.

DETAILED DESCRIPTION

Figure 1:
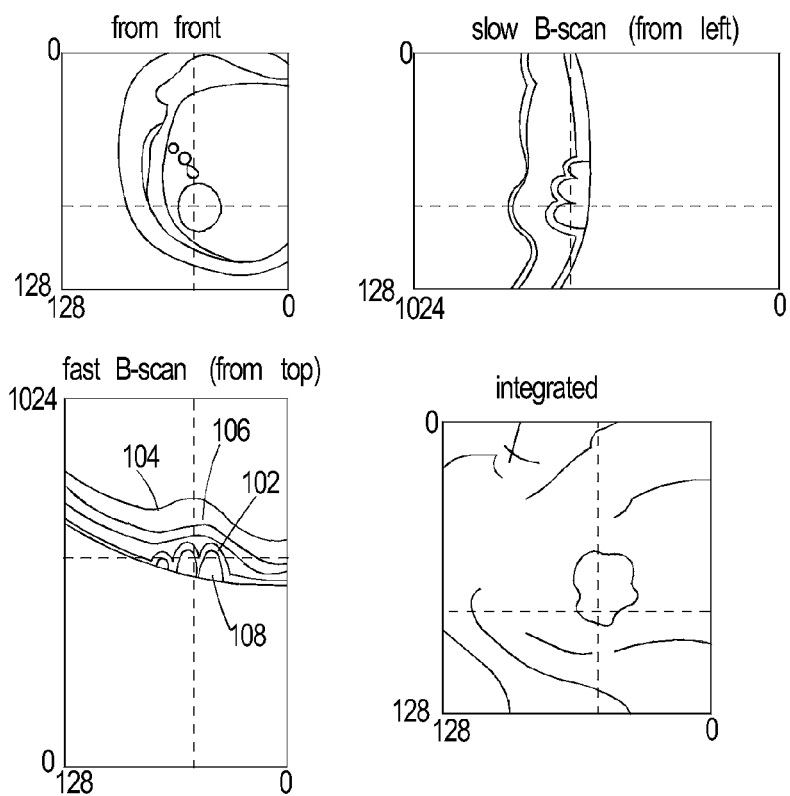
FIG. 1 shows OCT images of a retina, illustrating RPE (retinal pigment epithelium), the ILM (inner limiting membrane), a sharp bump and a lesion below the sharp bump.
Figure 2:
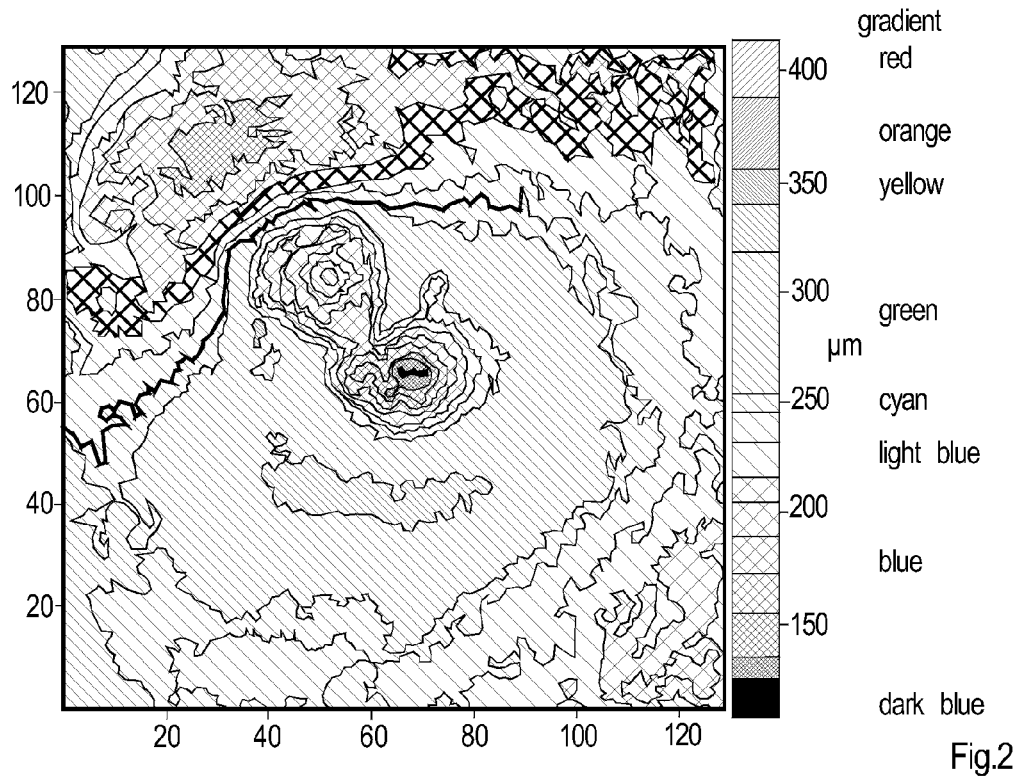
FIG. 2 is a color coded retina thickness map corresponding to FIG. 1.
Figure 3:
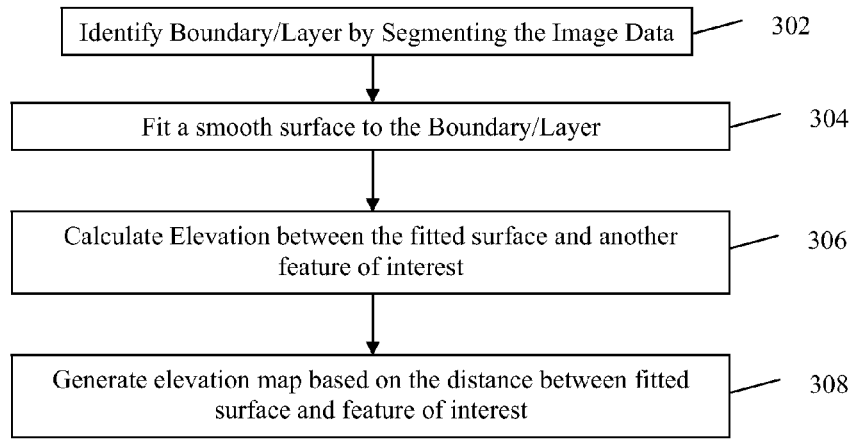
FIG. 3 shows a flow diagram of the steps of the invented image processing method.

FIG. 3 shows one preferred embodiment the presently invented method. This method is intended to be used on image data obtained from a sample. The illustrations in this application are based on image data derived from an optical coherence tomography system (OCT) which includes both time domain and spectral domain OCT systems. Such an instrument generates 3D intensity data corresponding to an axial reflection distribution arising from reflecting features in the eye. As noted above, this information is currently used by doctors to view and diagnosis various pathologies in the eye. A basic OCT system will be discussed below.

Although the illustrated embodiments are limited to OCT data, the image processing concepts described herein may be used with 3D image data derived from other modalities. For example, image data may be created using various forms of confocal microscopy and even ultrasound imaging modalities.

The first step in the subject method requires identification of a subset of the image data which corresponds to a boundary surface within the sample (step 302). As used herein, boundary surface can be a limiting surface in the sample, a surface of a layer or other interface. The boundary should have a sufficient linear or 2D extent that it can be reasonably fitted to a geometric line or surface. In one embodiment of the present invention, the boundary surface is the cornea. In another embodiment of the present invention, the boundary surface is the retina.

Identification of the image data corresponding to a boundary surface is performed using a segmenting function. Methods for finding and segmenting a desired tissue layer or boundary surface are well-known in the art. (see for example, H. Ishikawa, et al., (2005) "Macular Segmentation with Optical Coherence Tomography". *Invest Ophthalmol Vis Sci.;* 46: 2012-201).

Once the image data corresponding to the selected surface has been segmented, the boundary is fitted to a substantially smooth reference surface (step 304). There are a number of well-known methods for fitting a measured surface data points to a geometric surface. One example is a second-order polynomial fit. Other functions, including Zernike or Chebyshev polynomials, Bessel functions, or a portion of a sphere or spheroid, can also be used for surface fitting. A smooth reference surface can be formed by fitting the shape of a tissue layer/boundary with a function of two variables. This requires a reasonably accurate segmentation of the chosen tissue layer/boundary and can be accomplished using, for example, a low-order polynomial fit in x and y.

The fitting may encompass the entire tissue layer/boundary or may be performed on various regions of the surface, e.g., fitting the foveal pit separately from the macula, or excluding pathological regions from the fitting. The reference surfaces can be used to define layers in the data that have the retinal tilt and curvature removed. In one aspect of the invention, these data points can be used to form en-face images representing retinal structures in those layers. This presents an advantage over the flat C-scan presentation of the data when imaging the curved layers in the anatomy of the eye, since a C-scan will only show tangential slices of the retinal layers.

As noted above, use of such a fitted surface can minimize the perturbations of the surface associated with disease so as to approximate the tissue surface that would exist if the tissue were normal. In this case, the fitting algorithm will function to reject points that are associated with the selected boundary surface but exist as a result of the disease. By using such a fitted surface, either of the tissue boundary being measured, or a different boundary, the effect of disease or injury is isolated from the overall shape of the tissue of interest, providing improved diagnostic information.

In the next step of the method (306), the distances or elevations between points on the reference surface and some other feature of interest are calculated. The feature of interest may be the actual boundary initially selected so that elevations will correspond to the deviations between the selected surface and the associated reference surface. The feature of interest can also be another interface or boundary within the sample.

Figure 5:
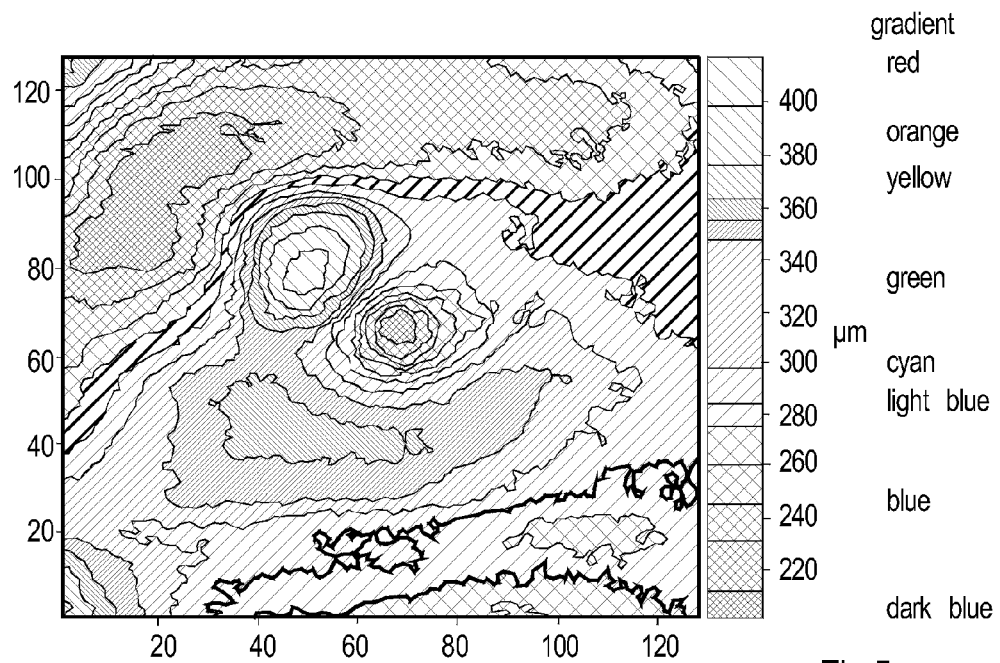
FIG. 5 shows a contour plot using the color coding that represents the distance from the ILM to a paraboloid fitted RPE reference surface.
Figure 6:
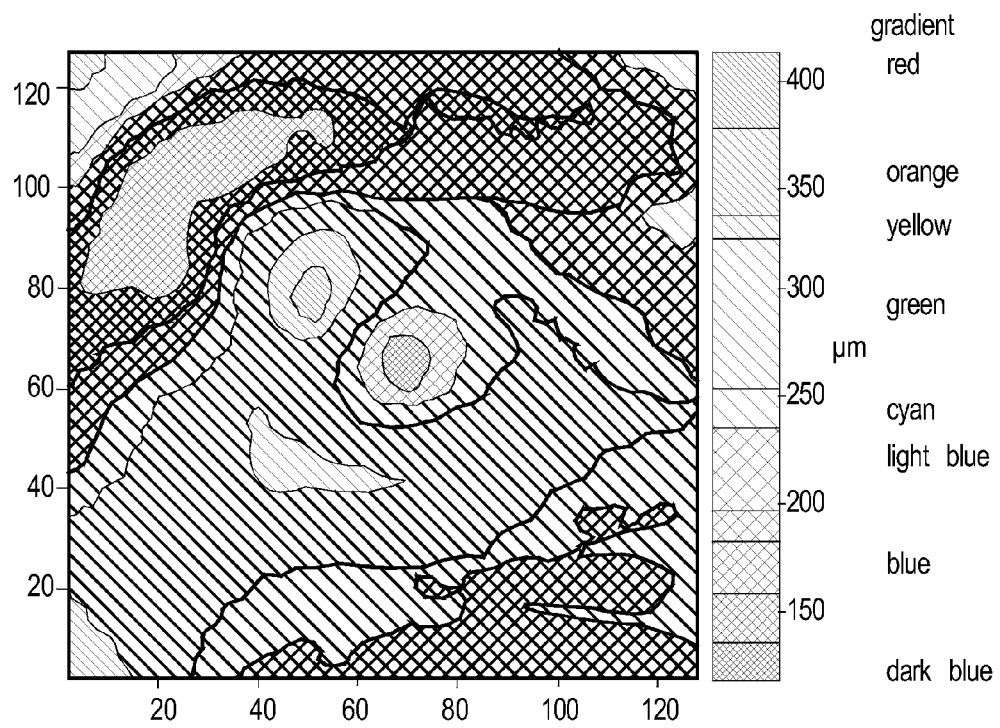
FIG. 6 shows a pseudocolor image representing the distance from the ILM to a paraboloid fitted RPE reference surface.

In the next step of the subject invention (308), 2D data sets are generated based on the calculated distances between the reference surface and other feature of interest. The 2D data sets can be used to create elevation maps. The elevation maps may be created based on pseudocolor or gray scales with elevation encoded as color as shown in FIG. 6 or intensity (not shown); or as topographical contour maps with elevation encoded as contour height as shown in FIG. 5 or as three dimensionally rendered topographical maps. These types of maps may also be combined to simultaneously display on the same map two sets of data, one for elevation relative to a fitted reference surface and the other for either another elevation relative to another reference surface, or an actual tissue layer thickness, or the originally collected image signal strength such as OCT or confocal optical signal strength for a tissue layer or other processed/unprocessed tissue layer/boundary data such as birefringence measured from a polarization sensitive OCT system or a scanning laser polarimetry system. For example, the distance from ILM relative to the RPE (i.e. the actual retina thickness) could be displayed as a contour map superimposed on a pseudocolor map of ILM elevation relative to a fitted RPE reference surface (not shown). Similarly, a pseudocolor map may be applied to a three-dimensional surface rendering in order to simultaneously display multiple information on elevation, thickness, reflectance or others.

In addition to the fact that by analyzing the curvature of the fitted reference surface, abnormal tissue layer curvatures (for example, the retina curvature for the case of pathologic myopia) can be diagnosed, the present invention has a number of other advantages over prior art methods as it can provide additional useful information for diagnosing diseased tissues. For example, the fitted reference surface can be used as a basis for elevation maps of retinal layers, to diagnose abnormal curvature of the retina, or as a guide for subsequent contour-following scans of that eye. Using such a fitted reference surface as a basis for "thickness" measurements could give more robust results because the exact topography of a deteriorating RPE may be more difficult to determine than the general shape of that layer. The reference surface determined by fitting will be more consistent than that determined by following the RPE in detail, especially in diseased eyes that may have breaks or complex variations in the RPE. As an example, map(s) of elevation can be displayed in the form of topographical contour map(s) applied to surface renderings of elevation. FIG. 5 shows a color contour coding that represents the distance from the ILM to a paraboloid reference surface fitted to the RPE. The corrected effective retinal "thickness" relative to the fitted surface is shown in microns on the color bar to the right of the map.

Figure 10:
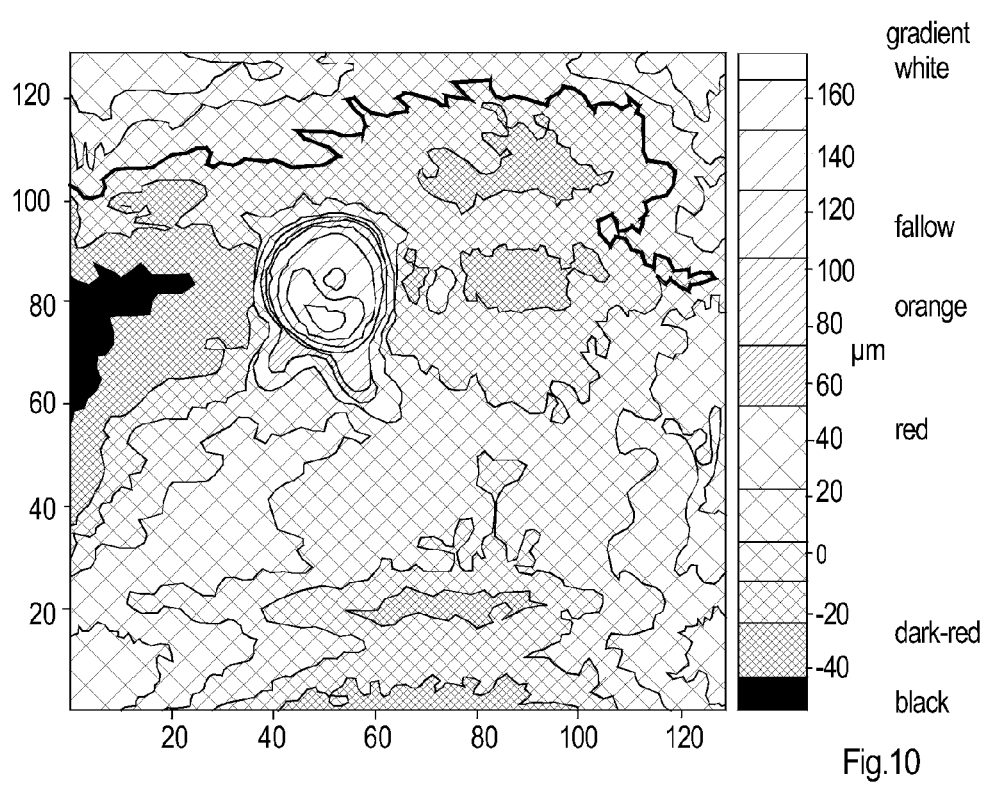
FIG. 10 shows a pseudocolor image representing the distance from the RPE to a paraboloid fitted RPE reference surface.

Additionally, presentation of topographic information relative to a fitted reference surface or surfaces can generate images with added information, for example:

(1) a 2-D false color image giving an en-face presentation of distance from the ILM to a reference surface fitted to the RPE can provide information on the effective retinal thickness which does not include thickness variations caused by small perturbations in the RPE. FIG. 6 shows a pseudocolor image representing the distance from the ILM to a paraboloid fitted RPE reference surface;

(2) a 2-D false color image giving an en-face presentation of distance from the actual RPE to a reference surface fitted to the RPE itself can highlight localized variations in the RPE which may be associated with disease. FIG. 10 shows a pseudocolor image representing the distance from the RPE to a paraboloid fitted RPE reference surface.

Figure 4:
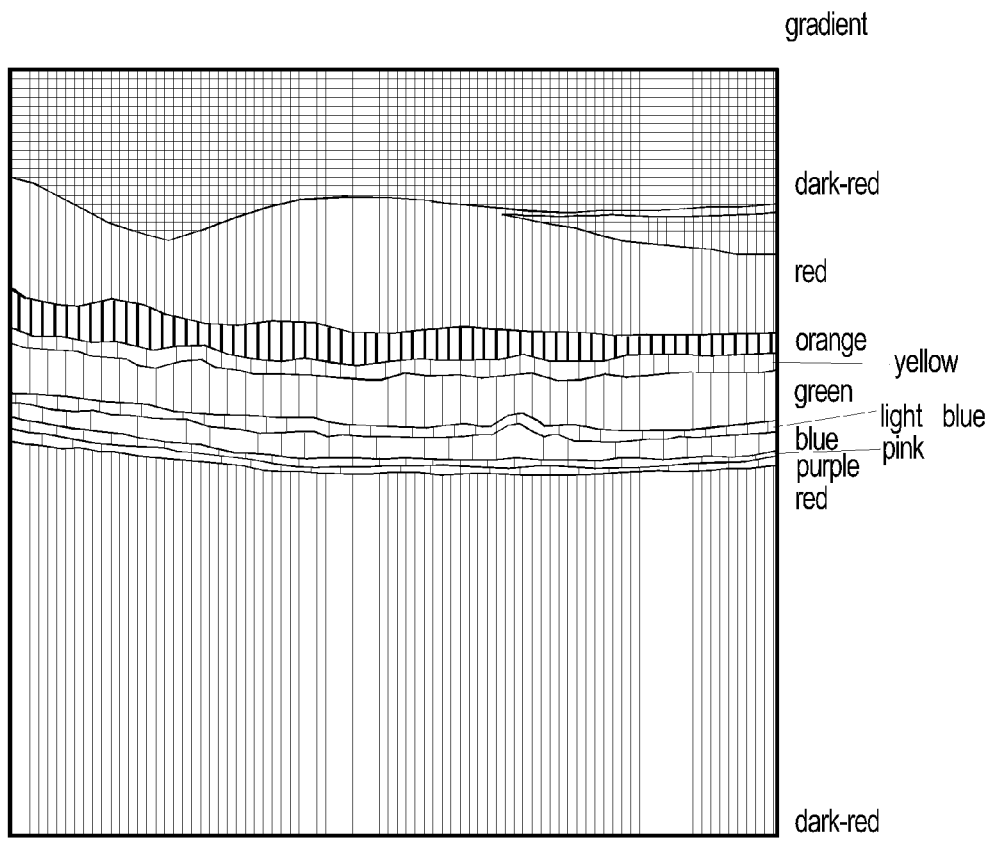
FIG. 4 shows a retina image with the hue mapped as the square of the distance from the fitted RPE reference surface.

(3) a color mapping for 2-D images or translucent 3-D renderings, in which brightness represents reflectance and hue represents distance from the reference surface, can provide an illustration of the height of brightly reflecting layers from the reference surface without detailed segmentation of all the layers. For cases of complicated pathology, fully automated segmentation algorithms for multiple layers may be too time-consuming for routine use and manual user intervention may not be practical. For example, in the case of an RPE detachment, the layers that are normally brightly reflecting very near to the reference surface are now very far removed from the reference surface. The human eye is very sensitive to hue changes, and a convenient way to illustrate such RPE detachment is to use hue changes. FIG. 4 shows a 2-D retina image with the hue mapped as the square of the distance from the fitted RPE reference surface.

Figure 7:
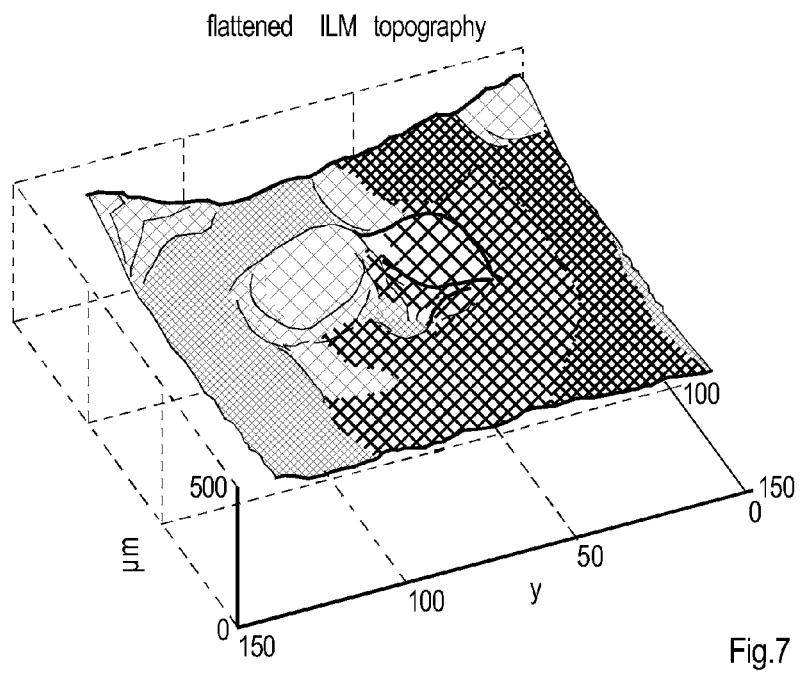
FIG. 7 shows a three-dimensional rendering of the ILM surface elevation relative to the paraboloid fitted RPE reference surface, with the color indicating in duplicate the same elevation information.

(4) a flattened 3-D rendering of a retinal surface or surfaces, which shows the elevation relative to a reference surface rather than its actual contour elevation in the image data can provide a more meaningful view of the retina anatomic features. FIG. 7 shows a three-dimensional rendering of the ILM elevation relative to a paraboloid fitted RPE reference surface. Different pupil positions cause tilt in the recorded retinal images, and variations in working distance cause different curvature in the recorded retinal images. Warping the OCT data to flatten this image may have advantages for more standardized presentation, regardless of exact pupil and z position, aiding comparisons of the images between visits, or registration of multiple scans for other purposes such as speckle reduction.

Figure 8:
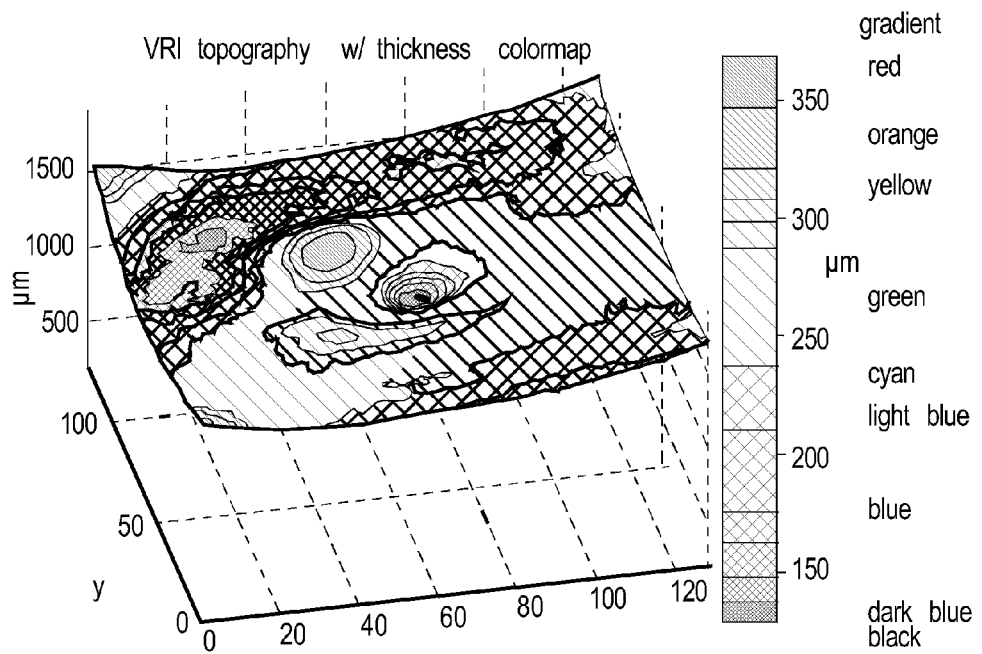
FIG. 8 shows a three-dimensional rendering of the actual retina thickness superimposed with a pseudocolor image indicating ILM elevation with respect to the paraboloid fitted RPE reference surface.
Figure 9:
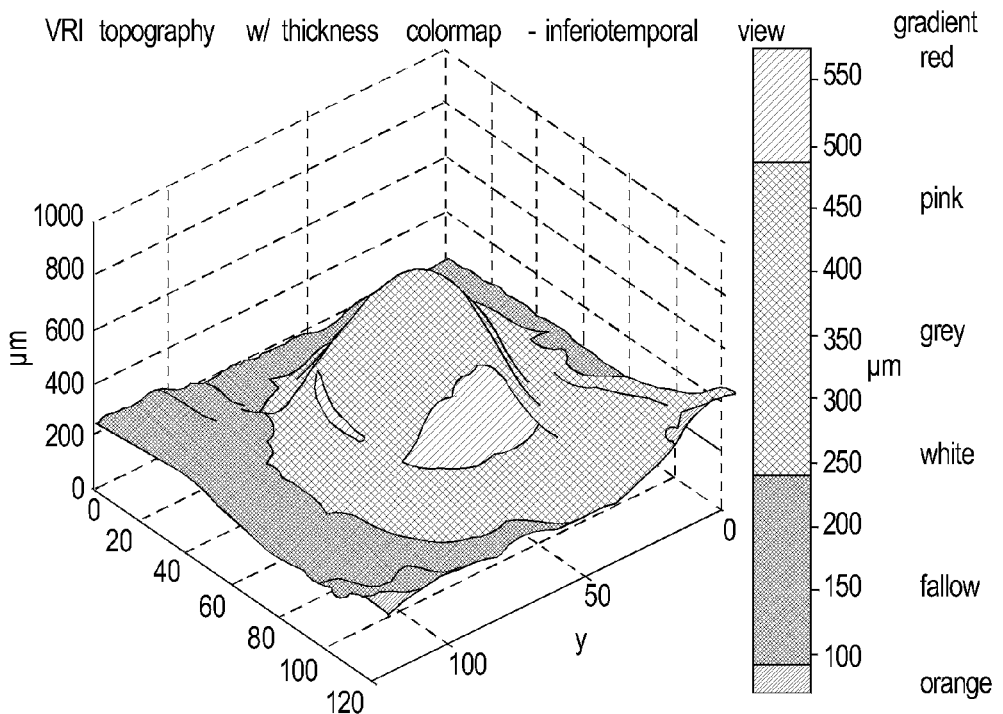
FIG. 9 shows a three-dimensional rendering of the ILM surface elevation relative to the paraboloid fitted RPE reference surface superimposed with a pseudocolor image indicating actual retinal thickness.

(5) a 3-D rendering of the ILM with a color mapping for elevation relative to the reference surface fitted to the RPE can combine the false color image previously described in (1), along with the actual retina thickness which could indicate the presence of traction by membranes on its surface. FIG. 8 shows a three-dimensional rendering of the actual retina thickness superimposed with a pseudocolor image indicating ILM elevation with respect to the paraboloid fitted RPE reference surface. On the other hand, such a superimposed 3D rendering can also be the other way round. For example, FIG. 9 shows a three-dimensional rendering of the ILM surface elevation relative to the paraboloid fitted RPE reference surface superimposed with a pseudocolor image indicating actual retinal thickness. The ILM elevation may reflect the position in the image data or a rendering that is flattened to a reference surface as previously described in (4).

Axial resolution may be wasted if the z-range of the scan does not follow the contour of the retinal tissue. A few initial scans could be used to determine the reference surface, then a retina-following scan could be performed by changing the OCT reference arm length to follow the predetermined reference surface as the transverse scans are performed.

Note that the present invention can also be applied to B-scan images in which case, the term reference surface should interpreted as a reference curved line and tissue layer/boundary will also be interpreted as a curved line. FIG. 4 shows a B-scan retina image with the hue mapped as the square of the distance from the fitted RPE reference surface. The vertical distance in the image relative to the location of the fitted RPE reference surface is encoded as a color which is used to highlight the image.

The present invention does not need to follow the exact sequence as shown in FIG. 3, as other additional steps can be inserted to perform substantially equivalent operations. For example, the fitting operation may be approximated by smoothing or otherwise filtering the retinal layer. Also, the reference surface might not be the direct result of fitting, but some filtered version thereof. Furthermore, a variation of this idea could use two such reference surfaces, rather than the elevation from an unfitted surface to a reference surface.

The presently invented method could be applied to the analysis of the retina or curvature of the eye in existing and future OCT systems. It can also be used for analysis of other biological tissues such as the skin. Also, it may find use in ultrasound and confocal microscopy systems as well.

Figure 11:
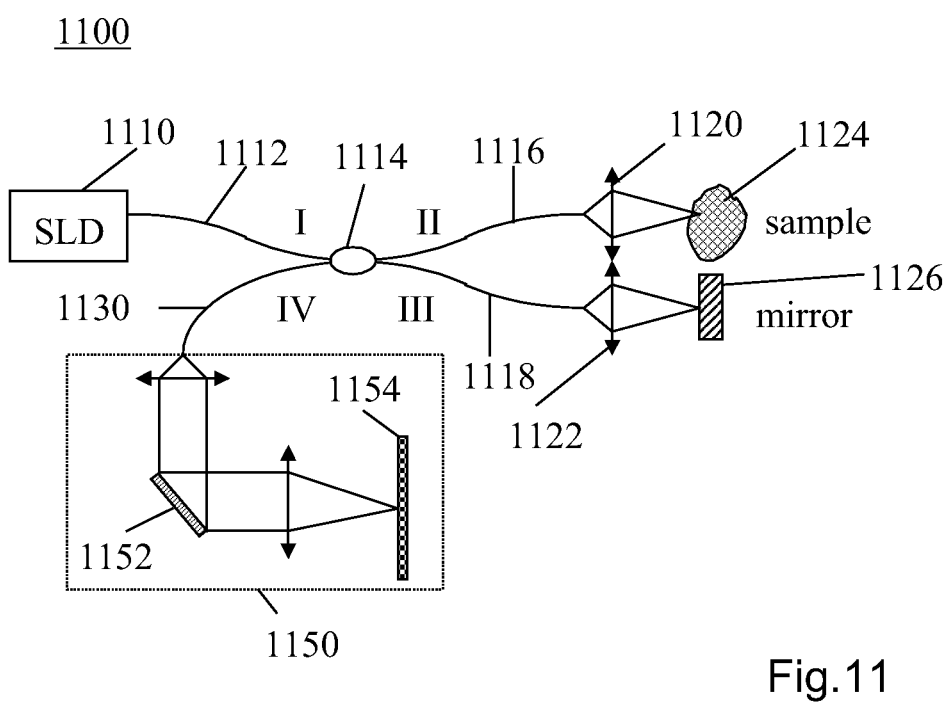
FIG. 11 is a schematic diagram of a basic OCT system capable of generating 3D image data that can be used in the method of the subject invention.

FIG. 11 shows a basic spectrometer based spectral domain OCT system 1100. The light wave from the broadband emitter 1110 is preferably coupled through a short length of an optical fiber 1112 to an input port (port I) of a fiber optic coupler 1114, which splits the incoming light beam into the two arms of a Michelson interferometer. The two arms each have a section of optical fiber (1116 and 1118) that guides the split light beam from the two output ports (port II and port III) of the fiber coupler 1114 to a sample 1124 and a reference reflector 1126 respectively. For both the sample arm and the reference arm, at the terminating portion of each fiber, there may be a module containing optical elements to collimate or focus or scan the beam. Illustrated in FIG. 11 as an embodiment are two focusing lenses 1120 and 1122. The returned light waves from the sample 1124 and the reference reflector 1126 are directed back through the same optical path of the sample and reference arms and are combined in fiber coupler 1114. A portion of the combined light beam is directed through a section of optical fiber 1130 from port IV of the fiber coupler 1114 to a spectrometer 1150. Inside the spectrometer, the light beam is dispersed by a grating 1152 and focused onto a detector array 1154. Note that the principle of operation of a tunable laser based swept source OCT is very similar to that of a spectrometer based spectral domain OCT system (see for example, Choma, M. A. et al. (2003). "Sensitivity advantage of swept source and Fourier domain optical coherence tomography." *Optics Express* 11 (18): 2183-2189), hence the spectral domain OCT system for obtaining the 3D image data set can also be a swept source OCT system.

Although various embodiments that incorporate the teachings of the present invention have been shown and described in detail herein, those skilled in the art can readily devise many other varied embodiments that still incorporate these teachings.

The following references are hereby incorporated by reference:

US PATENT DOCUMENTS

U.S. Pat. No. 4,838,679
U.S. Pat. No. 5,293,871
U.S. Pat. No. 5,562,095
U.S. provisional patent application Ser. No. 60/632,387

OTHER PUBLICATIONS

Adaikkappan, M. et al., (2002) "Evaluation of Carotid Atherosclerosis by B-Mode Ultrasonographic Study in Hypertensive Patients Compared with Normotensive Patients" *Ind J Radiol Imag;* 12:3:365-368.

Bartsch, D. G. et al., (2004) "Optical coherence tomography: interpretation artifacts and new algorithm", *Proc. SPIE Medical Imaging* 2004: *Image Processing,* 5370: 2140-2151.

Choma, M. A. et al. (2003). "Sensitivity advantage of swept source and Fourier domain optical coherence tomography." *Optics Express* 11 (18): 2183-2189

Ishikawa, H. et al., (2005) "Macular Segmentation with Optical Coherence Tomography". *Invest Ophthalmol Vis Sci.;* 46: 2012-201.

Webb, R. H. (1996) "Confocal optical microscopy" *Rep. Prog. Phys.* 59 427-471.

Zhou, Q. et al. (2004). "Mapping retinal thickness and macular edema by high-speed three-dimensional optical coherence tomography". Ophthalmic Technologies XIV, SPIE, 5314: 119-125.

We claim:

1. A method for analyzing optical coherence tomography data of an eye, said eye having at least one boundary surface associated therewith, said method comprising:
   acquiring a set of image data of the eye using an optical coherence tomography (OCT) device, said device including a light source, a beam splitter for dividing the light along a sample arm and a reference arm, said sample arm further including optical elements to scan the beam over the eye, said OCT device including a detector for receiving light returned from both the sample and the reference arms and generating signals corresponding to 3D image data based on an axial reflection distribution arising from reflecting features in the eye;
   segmenting the 3D image dataset to identify the retinal pigment epithelium (RPE);
   generating a substantially smooth reference surface from the RPE;
   segmenting the 3D image dataset to identify an additional retinal surface;
   calculating the distance between points on the substantially smooth reference surface to points on the at least one additional segmented retinal surface;
   generating an image map of the calculated distances; and
   displaying the map or an analysis derived therefrom.

2. A method as recited in claim 1, wherein the substantially smooth reference surface minimizes the perturbations of the surface associated with disease so as to approximate the tissue surface that would exist if the tissue were normal.

3. A method as recited in claim 1, wherein the substantially smooth reference surface is generated using one or more portions of the RPE.

4. A method as recited in claim 1, wherein the substantially smooth reference surface is generated using the entire RPE.

5. A method as recited in claim 1, wherein the segmenting step identifies the inner limiting membrane (ILM).

6. A method as recited in claim 1, wherein the substantially smooth reference surface is generated by fitting the RPE.

7. A method as recited in claim 1, wherein the substantially smooth reference surface is generated by smoothing the RPE.

8. A method as recited in claim 1, wherein the substantially smooth reference surface is generated by filtering the RPE.

9. A method for analyzing optical coherence tomography data of an eye, said eye having at least one boundary surface associated therewith, said method comprising:

acquiring a set of image data of the eye using an optical coherence tomography (OCT) device, said device including a light source, a beam splitter for dividing the light along a sample arm and a reference arm, said sample arm further including optical elements to scan the beam over the eye, said OCT device including a detector for receiving light returned from both the sample and the reference arms and generating signals corresponding to 3D image data based on an axial reflection distribution arising from reflecting features in the eye;

identifying a boundary surface within the 3D image data set;

excluding at least one portion of the boundary surface;

generating a reference surface over the remaining regions of the boundary surface;

calculating the distance between points on the smooth reference surface to points of interest within the eye identified from the 3D image data set; and displaying or storing an image map of the calculated distances.

10. A method as recited in claim 9, wherein the points of interest correspond to points on said boundary surface.

11. A method as recited in claim 9, wherein the points of interest correspond to points on a different boundary surface.

12. A method as recited in claim 9, wherein the boundary surface is the cornea.

13. A method as recited in claim 9, wherein the boundary surface is identified using a segmentation function.

14. A method as recited in claim 9, wherein the substantially smooth reference surface is generated by fitting the boundary surface.

15. A method as recited in claim 9, wherein the substantially smooth reference surface is generated by smoothing the boundary surface.

16. A method as recited in claim 9, wherein the substantially smooth reference surface is generated by filtering the boundary surface.

17. A method as recited in claim 9, the at least one portion excluded from the boundary surface is a pathological region.

18. A method as recited in claim 9, wherein the substantially smooth reference surface approximates the tissue surface that would exist if the tissue were normal.

* * * * *

UNITED STATES PATENT AND TRADEMARK OFFICE
CERTIFICATE OF CORRECTION

PATENT NO. : 8,913,793 B2  
APPLICATION NO. : 13/787557  
DATED : December 16, 2014  
INVENTOR(S) : Matthew J. Everett et al.

Page 1 of 1

It is certified that error appears in the above-identified patent and that said Letters Patent is hereby corrected as shown below:

On Title page 2, in column 2, References cited under "Other Publications", line 37, delete "Investigatative" and insert -- Investigative --, therefor.

On Title page 3, in column 1, References cited under "Other Publications", line 14, delete "Coherencetomography"," and insert -- Coherence tomography", --, therefor.

On Title page 3, in column 1, References cited under "Other Publications", line 49, delete "on on" and insert -- on --, therefor.

On Title page 4, in column 1, References cited under "Other Publications", line 35, delete "Distrubution" and insert -- Distribution --, therefor.

In the Specification

In column 8, line 13, delete "2189" and insert -- 2189. --, therefor.

Signed and Sealed this  
Seventh Day of April, 2015

Michelle K. Lee  
*Director of the United States Patent and Trademark Office*